(12) United States Patent
Loeb et al.

(10) Patent No.: US 7,096,053 B2
(45) Date of Patent: Aug. 22, 2006

(54) INTERNAL BIOCHEMICAL SENSING DEVICE

(75) Inventors: Gerald E. Loeb, South Pasedena, CA (US); Thomas George, La Canada, CA (US)

(73) Assignee: Alfred E. Mann Institute for Biomedical Engineering at the University of Southern California, Los Angeles, CA (US)

( * ) Notice: Subject to any disclaimer, the term of this patent is extended or adjusted under 35 U.S.C. 154(b) by 0 days.

(21) Appl. No.: 10/263,272

(22) Filed: Oct. 2, 2002

(65) Prior Publication Data

US 2003/0171666 A1 Sep. 11, 2003

Related U.S. Application Data

(60) Provisional application No. 60/326,908, filed on Oct. 2, 2001.

(51) Int. Cl.
*A61B 5/00* (2006.01)

(52) U.S. Cl. ........................................ 600/317; 600/342

(58) Field of Classification Search ........ 600/309–310, 600/317, 312, 322, 342; 435/41, 325; 204/403.01–403.15
See application file for complete search history.

(56) References Cited

U.S. PATENT DOCUMENTS

| | | | | |
|---|---|---|---|---|
| 3,847,483 | A | * | 11/1974 | Shaw et al. .................... 356/41 |
| 4,929,561 | A | | 5/1990 | Hirschfeld |
| 4,974,929 | A | * | 12/1990 | Curry ............................ 385/12 |
| 4,981,779 | A | * | 1/1991 | Wagner ..................... 422/82.09 |
| 5,002,054 | A | * | 3/1991 | Ash et al. .................... 600/347 |
| 5,028,395 | A | | 7/1991 | Sebille et al. |
| 5,045,282 | A | | 9/1991 | Kritzman et al. |
| 5,079,421 | A | * | 1/1992 | Knudson et al. ............. 250/343 |
| 5,094,819 | A | | 3/1992 | Yager et al. |
| 5,096,671 | A | * | 3/1992 | Kane et al. ............... 422/82.07 |
| 5,098,659 | A | * | 3/1992 | Yim et al. ................ 422/82.07 |
| 5,109,442 | A | * | 4/1992 | Klainer et al. ................. 385/12 |
| 5,168,156 | A | | 12/1992 | Fischer et al. |
| 5,244,813 | A | | 9/1993 | Walt et al. |
| 5,279,295 | A | * | 1/1994 | Martens et al. ............. 600/335 |
| 5,309,537 | A | * | 5/1994 | Chun et al. .................... 385/59 |
| 5,341,805 | A | * | 8/1994 | Stavridi et al. .............. 600/316 |

(Continued)

OTHER PUBLICATIONS

Buck, R.P. Biosensor Technology : Fundamentals and Applications, (1990), M. Dekker, New York pp. 209-309.

(Continued)

*Primary Examiner*—Eric F. Winakur
(74) *Attorney, Agent, or Firm*—McDermott Will & Emery LLP (57) ABSTRACT

A biosensing device for detecting biological analytes, and methods of use and manufacture, are disclosed. The device includes a biosensing element that can remain implanted for extended periods of time. The biosensing element is connected to an optical fiber terminating outside of the body. The optical fiber is also connected to an information analyzer. The information analyzer directs light through the optical fiber into the biosensing element. The light excites fluorophores, created by a chemical reaction between analytes and biosensing material within the biosensing element. Emitted fluorescent light is redirected through the optical fiber to the information analyzer. Optical gratings within the filtering member of the information analyzer selectively deflect fluorescent emissions into a cladding layer. Detectors attached to the cladding layer detect the deflected fluorescent emissions and, according to their determined wavelength, report the presence or quantity of specific analytes to the patient on an external display.

10 Claims, 4 Drawing Sheets

U.S. PATENT DOCUMENTS

| | | | |
|---|---|---|---|
| 5,368,028 A * | 11/1994 | Palti | 600/345 |
| 5,408,999 A | 4/1995 | Singh et al. | |
| 5,483,958 A * | 1/1996 | Merberg et al. | 600/321 |
| 5,498,549 A | 3/1996 | Nagel et al. | |
| 5,605,152 A * | 2/1997 | Slate et al. | 600/316 |
| 5,632,958 A | 5/1997 | Kane et al. | |
| 5,706,807 A * | 1/1998 | Picha | 600/345 |
| 5,800,545 A | 9/1998 | Yamada et al. | |
| 5,881,188 A | 3/1999 | Starodubov | |
| 5,903,690 A | 5/1999 | Starodubov et al. | |
| 5,938,595 A * | 8/1999 | Glass et al. | 600/342 |
| 5,972,542 A | 10/1999 | Starodubov | |
| 5,982,963 A | 11/1999 | Feng et al. | |
| 6,002,822 A * | 12/1999 | Strasser et al. | 385/48 |
| 6,002,954 A * | 12/1999 | Van Antwerp et al. | 600/317 |
| 6,011,984 A | 1/2000 | Van Antwerp et al. | |
| 6,058,226 A | 5/2000 | Starodubov | |
| 6,063,637 A | 5/2000 | Arnold et al. | |
| 6,095,974 A * | 8/2000 | Shemwell et al. | 600/310 |
| 6,103,535 A | 8/2000 | Pilevar et al. | |
| 6,210,910 B1 | 4/2001 | Walt et al. | |
| 6,222,973 B1 | 4/2001 | Starodubov | |
| 6,241,691 B1 * | 6/2001 | Ferrera et al. | 600/585 |
| 6,310,998 B1 | 10/2001 | Starodubov | |
| 6,319,540 B1 | 11/2001 | Van Antwerp et al. | |
| 6,331,163 B1 * | 12/2001 | Kaplan | 600/486 |
| 6,344,298 B1 | 2/2002 | Starodubov et al. | |
| 6,417,506 B1 * | 7/2002 | Pinkel et al. | 250/216 |
| 6,442,305 B1 | 8/2002 | Starodubov et al. | |
| 6,453,095 B1 | 9/2002 | Feng et al. | |
| 6,485,413 B1 * | 11/2002 | Boppart et al. | 600/478 |
| 6,505,059 B1 * | 1/2003 | Kollias et al. | 600/316 |

OTHER PUBLICATIONS

Claremont, D.J. et al. *In vivo* chemical sensors and biosensors in clinical medicine. In Turner, A.P.F. et al. Biosensors: Fundamentals and Applications. 1987, Oxford Science Publications, London, pp. 356-376.

Hogen-Esch et al., "Synthesis and Characterization of Well Defined End-Functionalized Hydrocarbon and Perfluorocarbon Derivatives of Polyethyleneglycol and Poly(N.N-dimethylacrylamide)", Chapter 11, in "Associative Polymers in Aqueous Solutions," (2000), ACS Symposium Series vol. J.E. Glass Editor 765, pp. 179-203.

Krohn, D.; Fiber Optic Sensors: Fundamentals and Applications. (1988), Instrument Society of America, North Carolina. pp. 203-223.

Mansouri et al. A Miniature Optical Glucose Sensor Based on Affinity Binding. Biotechnology 1984, 885-890.

Meadows, D.L. et al. Design, manufacture and characterizaton of an optical fiber glucose affinity sensor based on an homogeneous fluorescence energy transfer assay system. 1993. Analytica Chimica Acta, vol. 280: pp. 21-30.

Russell, R.J. et al. A fluorescence-based glucose biosensor using Concanavalin A and Dextran encapsulated in a poly(ethylene glycol) hydrogel. 1999. Analytical Chemistry, vol. 71: pp. 3126-3132.

Bardeletti, G. et al. Amperometric enzyme electrodes for substrate and enzyme activity determinations. In Biosensor Principles and Applications. 1991, M. Dekker; New York, pp. 7, 20-27.

Coulet, P.R. What is a Biosensor? In Biosensor Principles and Applications. 1991, M. Dekker; New York, pp. 1-6.

Czarnik, A.W. Supermolecular chemistry, fluorescence, and sensing. In Fluorescent Chemosensors for Ion and Molecule Recognition. 1993, American Chemical Society, Washington, D.C. ACS Symposium Series 538. pp. 1-9.

Fraser, D. An introduction to in vivo biosensing: progress and problems. In Fraser D. Biosensors in the body: continuous *in vivo* monitoring. 1997, Wiley, New York, pp. 10-56.

Hall, E.; Biosensors. 1991, Prentice Hall, New Jersey. Chapter 1, pp. 1-29, Chapter 2, pp. 30-47, Chapter 10, pp. 310-315, Chapter 6, pp. 172-175.

Koudekla-Hep, M. Electrochemical sensors for *in vivo* glucose sensing. In Fraser D. Biosensors in the body: continuous *in vivo* monitoring. 1997, Wiley, New York, pp. 57-77.

McKinney R.M. et al. A simple method for dtermining the labeling efficiency of fluorescein isothiocyanate products. 1966. Analytical Biochemistry vol. 14: 421-428.

McNichols, R.J. et al. Optical glucose sensing in biological fluids: an overview. 2000. Journal of Biomedical Optics, vol. 5, No. 1: pp. 5-16.

Munkholm, C. et al. Polymer modification of fiber optic chemical sensors as a method of enhancing fluorescence signal for pH measurement. 1986. Analytical Chemistry, vol. 58:1427-1430.

Russell, R.J. et al. Poly(ethylene glycol) hydrogel-encapsulated fluorophore-enzyme conjugates for direct detection of organophosphorus neurotoxins. 1999. Analytical Chemistry, vol. 71: pp. 4909-4912.

Schaffar, B.P.H. et al. Chemically mediated fiberoptic biosensors. In Biosensor Principles and Applications. 1991. M. Dekker; New York, pp. 163-194.

Schultz, J.S. Design of fibre-optic biosensors based on bioreceptors. In Turner, A.P.F. et al. eds. Biosensors: Fundamentals and Applications. 1987, Oxford Science Publications, London, pp. 638-654.

Szmacinsky, H. et al. Lifetime-based sensing using phase-modulation fluorometry. In Fluorescent Chemosensors for Ion and Molecule Recognition. 1993, American Chemical Society, Washington, D.C. ACS Symposium Series 538. pp. 196-213, 220-226.

Thompson, R.B. Fluorescence-based fiber-optic sensors. In Lakowicz, J.R., ed. Topics in Fluorescence Spectroscopy, vol. 2: Principles. 1991. Plenum Press, New York, pp. 345-365.

Wang, P. et al., "Surface modification of poly(tetrafluoroethylene) films via grating of poly(ethylene glycol) for reduction in protein adsorption." 2000. Journal of Biomedical Science and Polymer Edition. vol. 11: pp. 169-186.

* cited by examiner

INTERNAL BIOCHEMICAL SENSING DEVICE

CROSS REFERENCE TO RELATED APPLICATION

This application is related to and claims the benefit of the filing date of U.S. provisional application Ser. No. 60/326,908, filed Oct. 2, 2001, entitled "Percutaneous Photochemical Sensing Device and Method of Manufacture," the contents of which are incorporated herein by reference.

BACKGROUND OF THE INVENTION

1. Field of the Invention

The present invention relates generally to implanted devices and methods for repeated detection of biochemical analytes.

2. General Background and State of the Art

In order to detect or manage certain diseases or conditions, it is useful to make frequent measurements of specific biochemical analytes, hereinafter referred to as "analytes," within a patient's body over an extended period of time. For example, glucose levels in a patient's body can be monitored to guide the dosage of insulin required to treat diabetes mellitus. Another example would be monitoring the tissue concentration of therapeutic drugs such as anticoagulants, immunosuppressive agents and anticancer drugs, all of which can lead to serious complications if the tissue levels are too high or too low. Monitoring the presence and levels of such analytes in a patient's body is often a cumbersome process, making it difficult to accomplish over extended periods of time. For example, glucose monitoring is frequently performed through invasive means utilizing external glucose meters. Typically, glucose measurements are taken by pricking a patient's finger, extracting a drop of blood, and applying the blood to a test strip containing chemicals that are sensitive to the glucose in the blood sample. An optical meter is then used to analyze the blood sample on the test strip and provide the patient with a numerical glucose reading. Because readings show only a "snap shot" of blood glucose levels, repeated painful finger pricks are required over time. Also patients must carry supplies to take repeated measurements. These factors lead to patient non-compliance.

Less invasive methods for detecting analytes in a patient's body are known and practiced, but have limited effectiveness for other reasons. For example, certain transcutaneous optical absorption techniques for quantification of glucose can be based on selective absorption of light by the glucose molecule. However, such in vivo measurements are susceptible to inaccuracies due to differences in skin pigmentation, hydration, blood flow, probe placement and probe pressure. Because skin is a highly scattering medium, optical measurements taken through the skin are adversely affected by attenuation and low signal-to-noise ratio.

Thus, there is a need for a minimally invasive device and method for repeated detection of a broad range analytes from patients. There is also a need for a compact and portable, yet accurate system for detection.

SUMMARY

In one aspect of the present invention, a compact and portable biosensing device for detecting an analyte from within a patient's body, comprises a biosensing element including a biosensing material, an elongated transmitting member having a first end and a second end and being optically aligned with the biosensing element at the first end, and a portable information analyzer connected to the second end of the elongated transmitting member and sized and configured to be easily carried by the patient.

In another aspect of the invention, an information analyzer for sensing an analyte detected from within a patient's body comprises an elongated filtering member configured to propagate light and having a cladding layer along its length and having a first end and a second end, the elongated filtering member further including a wavelength specific grating region configured to deflect a portion of the propagated light having the specific wavelength into the cladding layer. The information analyzer further includes a connector operatively connected to the first end of the elongated filtering member and adapted to receive an optical fiber and form an optical connection therewith, a light source operatively connected to the second end of the elongated filtering member and configured to direct light therethrough, and a processor operatively connected to the cladding layer for detecting the deflected light.

In another aspect of the invention, a method of using a compact and portable biosensing device comprises inserting a biosensing element and a first end of an elongated transmitting member into a patient's body such that the first end of the elongated transmitting member is optically aligned with the biosensing element, and a second end of the elongated transmitting member remains outside of the patient's body, optically coupling the second end of the elongated transmitting member to a portable information analyzer, directing light from a light source through an elongated filtering member within the information analyzer and through the elongated transmitting member to the biosensing element, directing fluorescent energy from the biosensing element and activated by the directed light through the elongated transmitting member and through at least a part of the elongated filtering member, deflecting at least a portion of the fluorescent energy to a cladding layer adjacent to the elongated filtering member, and detecting the deflected fluorescent energy.

In yet another aspect of the invention, an adaptive system of biosensors for sensing a plurality of analytes comprises a first biosensor device comprising a first biosensing element and a first elongated transmitting member, a second biosensor device comprising second biosensing element and a second elongated transmitting member, and a first end of each of the first and second elongated transmitting members being optically connectable to a portable information analyzer, wherein the first biosensing element contains a first biosensing material that is different from a second biosensing material contained within the second biosensing element, and the first and second biosensing materials react with different ones of the plurality of analytes.

In still a further aspect of the invention, a method of manufacturing a compact and portable biosensing device comprises encapsulating a biosensing material within a region substantially adjacent to a first end of an elongated transmitting member by attaching a containment matrix to the first end of the elongated transmitting member such that it surrounds the biosensing material, providing a connector that will align a second end of the elongated transmitting member with a first end of an elongated filtering member such that they are optically connected, creating a wavelength specific optical grating in a portion of the elongated filtering member, and connecting a light detector to the elongated filtering member adjacent to the wavelength specific optical grating.

In another aspect of the invention, a compact and portable biosensing device for detecting an analyte from within a patient's body comprises a biosensing element for implantation in a patient's body including a biosensing material, an elongated transmitting member having a first end and a second end and a transmitting member outer surface, and the first end being implanted within a patient's body and the transmitting member being optically aligned with the biosensing element at the first end, and a portable information analyzer connected to the second end of the elongated transmitting member and configured to be carried externally to the patient's body.

One advantage of various embodiments of the invention is that problems associated with previous methods of repeatedly measuring patient analytes are avoided. For example, optical fibers are small, thin, lightweight, chemically stable and generally biocompatible, allowing them to be relatively easily inserted into a patient's body and maintained for repeated measures over time. Combined with fluorescence techniques for analyte detection, changes in fluorescence intensity and/or wavelength caused by binding of the analyte with a biosensing material, an optical fiber can transmit fluorescing evidence of the analyte from within the patient's body to an external analyzer.

The invention teaches the use of complementary new technologies for photonic signal processing that enable the construction of a light-weight, low-cost, robust photonic analyzer to be used with the implanted optical fiber sensors by the patient in the field or by a caregiver at bedside.

By way of example, this system may be useful in the monitoring of fluctuations in exogenous or endogenous hormone levels related to fertility treatments (such as timing of conception, egg-harvesting and implantation of in vitro fertilized embryos). Further, this system may be useful in monitoring critical care patients, detecting newly identified proteins whose presence signals deterioration of heart, liver, brain and other tissues that would justify more aggressive treatment and whose absence might justify less expensive care. This system may also be useful for monitoring levels of bioactive compounds that have narrow margins between safe and toxic levels (e.g., anticancer, immunosuppressive and anticoagulant drugs) or whose pharmacokinetics are uncertain (e.g., uncertain absorption, metabolism and excretion rates). Finally, the system may be useful in monitoring of metabolic indicators (e.g., oxygen concentration, pH, urea, lactate, etc.) in unstable patients (e.g., post-operative, post-trauma, complicated pregnancy). The sensing materials for these analytes could be based on antibodies, enzymes and other catalysts whose amount of specific binding or rate of reaction depends on the concentration of the analyte in the adjacent fluids.

It is understood that other embodiments of the present invention will become readily apparent to those skilled in the art from the following detailed description, wherein it is shown and described only exemplary embodiments of the invention by way of illustration. As will be realized, the invention is capable of other and different embodiments and its several details are capable of modification in various other respects, all without departing from the spirit and scope of the present invention. Accordingly, the drawings and detailed description are to be regarded as illustrative in nature and not as restrictive.

BRIEF DESCRIPTION OF THE DRAWINGS

Aspects of the present invention are illustrated by way of example, and not by way of limitation, in the accompanying drawings, wherein:

FIG. 5 illustrates an exemplary method for creating a multiple, tuned optical grating within the filtering member of the exemplary information analyzer.

DETAILED DESCRIPTION OF THE DRAWINGS

The detailed description set forth below in connection with the appended drawings is intended as a description of exemplary embodiments of the present invention and is not intended to represent the only embodiments in which the present invention can be practiced. The term "exemplary" used throughout this description means "serving as an example, instance, or illustration," and should not necessarily be construed as preferred or advantageous over other embodiments. The detailed description includes specific details for the purpose of providing a thorough understanding of the present invention. However, it will be apparent to those skilled in the art that the present invention may be practiced without these specific details. In some instances, well-known structures and devices are shown in block diagram form in order to avoid obscuring the concepts of the present invention.

Figure 1:
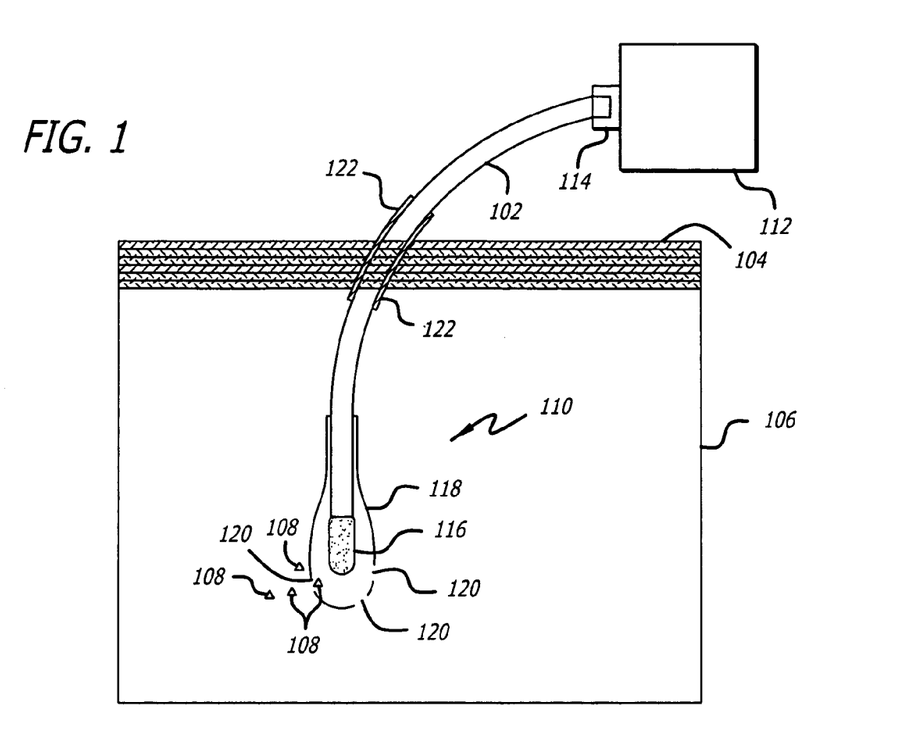
FIG. 1 illustrates a compact and portable biosensing device and an exemplary mode of positioning relative to a patient's body.

FIG. 1 illustrates a compact and portable biosensing device and an exemplary mode of positioning relative to a patient's body. The exemplary biosensing device comprises a transmitting member 102 that extends through the patient's skin 104. The transmitting member 102 may be injected in a percutaneous region of the patient's body 106, or in any other region in which analytes 108 are being tested. The biosensing device includes a biosensor element 110, attached to the end of the transmitting member 102 that is inserted into the patient's body. The opposite end of the transmitting member 102 may be attached to an information analyzer 112, by means of a connector 114. The information analyzer 112 receives information directed from the biosensing element 110 through the transmitting member 102, then filters and analyzes the received information to detect the presence or quantity of analytes within the patient's body 106.

In an exemplary embodiment, the transmitting member 102 is a single optical fiber. It is to be understood that the transmitting member might include additionally other channels required to initiate or modify the sensing function. For example, a second optical fiber might be incorporated to provide photonic excitation of a chemical or fluorescence reaction. In another example, a fine electrical wire might be incorporated to apply an electrical current or biasing voltage or to generate electrolysis of the body fluids to induce pH changes. In yet another example, a loop of electrical wire might be incorporated as a heating element. In yet another example, a capillary tube might be incorporated to allow introduction of a chemical enzyme or initiator of the reaction to be detected via an optical fiber in the transmitting member. The use of these various interfaces to initiate, control or modify a chemical reaction are well known in the art and are easily accommodated in the transmitting member without unduly increasing its diameter or stiffness.

The information transmitted through the optical fiber 102 is light energy (photons at different wavelengths), and the connector 114 is an optical connector, to ensure the presence of an optical connection between the optical fiber 102 and the information analyzer 112. In this embodiment, the information analyzer 112 exposes the biosensor element 110 to excitation light of a first wavelength that is directed through the optical fiber 102 to the biosensor element, and in response receives emitted fluorescent light of at least a second wavelength from the biosensor element 110, directed through the optical fiber 102 in the opposite direction. The emitted fluorescent light is then filtered and analyzed by the information analyzer 112 to identify and/or quantify the analytes detected by the biosensor element 110. The information analyzer 112 may identify the presence of specific analytes by measuring the wavelength of the fluorescent light emitted, and measures the quantity of analytes present by measuring the intensity of the fluorescent light emitted. The directing of these various forms of light, and the general configuration of the biosensor element 110, are now described in further detail.

The biosensor element 110 comprises biosensing material 116 located substantially at the end of the optical fiber 102. In a first exemplary embodiment, the biosensing material 116 may be attached directly to the internal end of the optical fiber 102. In an alternative exemplary embodiment, the biosensing material 116 may be inserted into the patient's body 106 separately from the optical fiber 102, and the optical fiber 102 positioned in proximity to the implanted biosensing material 116. In another exemplary embodiment, it may be desirable to prevent substantially direct contact between the biosensing material 116 and patient tissue 106. In this case, the biosensor element 110 includes a containment matrix 118 that substantially contains the biosensing material 116 within a reaction region that is in close proximity to the end of the optical fiber 102. Further, the containment matrix 118 may be configured to be in contact with or form a seal with the optical fiber 102. The containment matrix 118 thereby can contain the biosensing material so that it does not diffuse away from the biosensor element. The containment matrix 118 might also contain the products of a reaction between analytes 108 and the biosensing material 116. This containment of the reactive products can prevent them from dispersing throughout the patient's body such that they are retained within a concentrated area for signal communication to the optical fiber 102. The containment matrix 118 can include pores 120 to allow analytes 108 to diffuse within the containment matrix 118 to contact the biosensing material. The pores 120 may be inherently formed due to the characteristics of the material used for the containment matrix or, if the selected material is not sufficiently porous, then pores may be explicitly created therein, for example by burning holes using a tightly focused laser beam such as an excimer laser. The pores are sized such that they are large enough to allow the diffusion of analytes 108 into the reaction region, and small enough to prohibit the passage of other elements from the reactive region to other areas of the patient's body.

Figure 2:
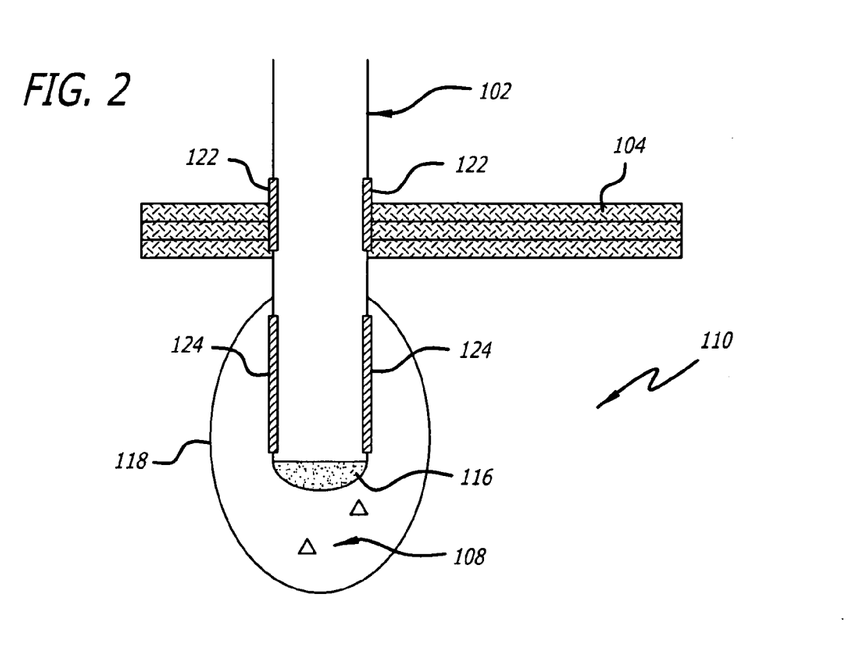
FIG. 2 illustrates an exemplary biosensing element configuration.

FIG. 2 illustrates an exemplary biosensor element 110 and certain other features of the exemplary biosensing device. The optical fiber 102 may be composed of a number of different materials such as, for example, glass, silicon or plastic. While different materials may be used in any of the embodiments described herein, glass has desirable optical properties and can be configured to have a silicon outer surface that can be modified to bind different coatings (discussed below). Although the optical fiber 102 does not have a specific size requirement, fibers having a diameter between about 50 µm and about 200 µm are used for ease of insertion through the skin 104 of a patient. Fibers within this range of sizes are also sufficiently large for effective data transmission, suitably flexible that a patient can manipulate them with ease, and sufficiently strong to withstand patient wear. For example, an unclad 50 µm glass fiber can be bent to a radius of about 2 mm before fracturing.

Figure 3:
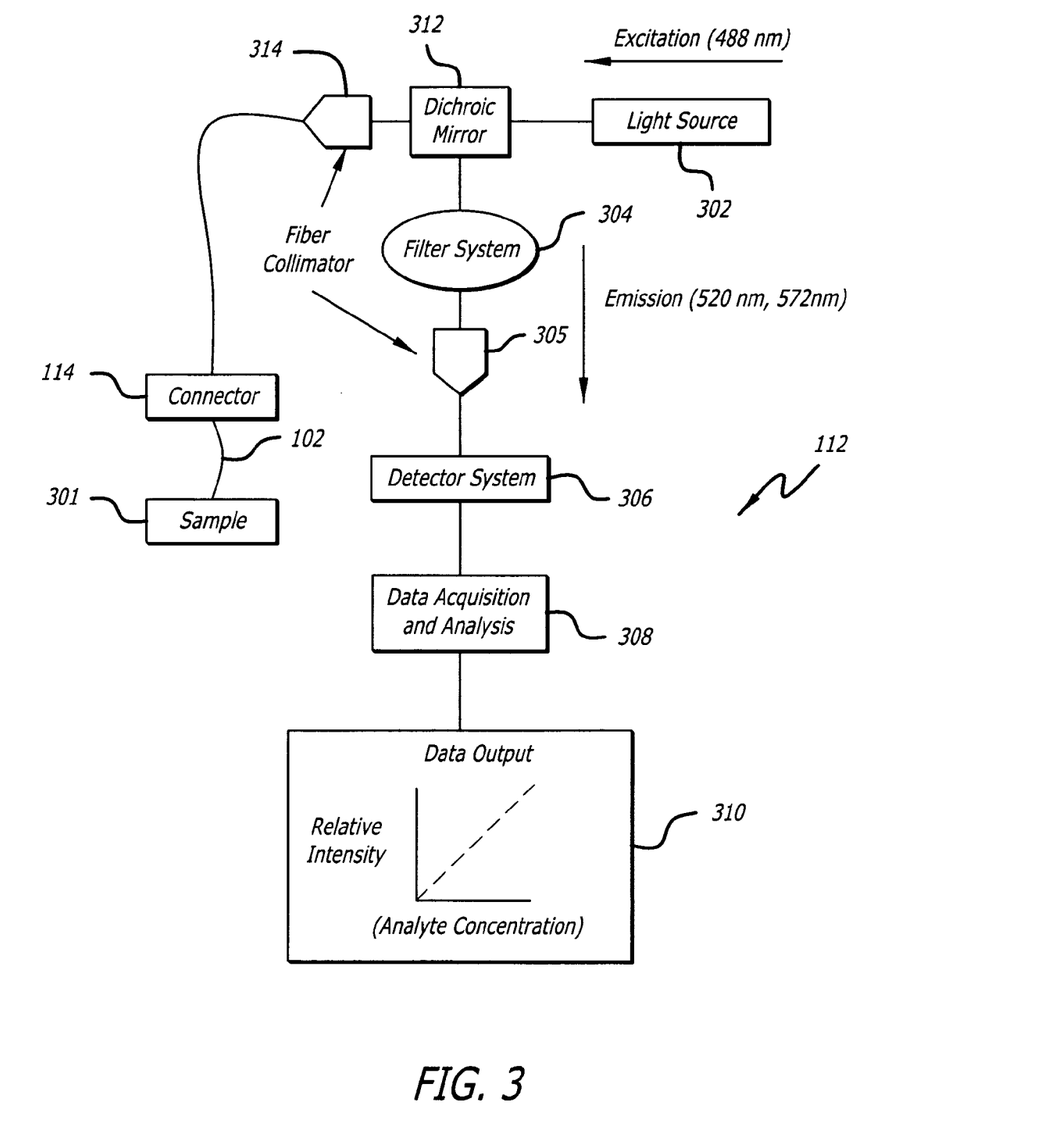
FIG. 3 is a functional block diagram of an exemplary information analyzer.

FIG. 3 is a functional block diagram of an exemplary information analyzer. In the exemplary embodiment, the information analyzer 112 is a photonic analyzer. Specifically, the information analyzer is a fluorescence spectrophotometer that photonically excites a sample 301 within, or in proximity to the biosensor element 110, and then detects the wavelength and/or intensity of any optical signal emitted therefrom. The information analyzer 112 includes a light source 302, one or more optical filters 304, a photon detector 306, signal processing electronics 308 and a patient readout system 310.

In an exemplary method employed by the information analyzer 112, an excitation wavelength is produced by light source 302. The light source 302 may be, for example, a fiber-coupled blue laser diode with a built-in source driver capable of producing, for example, 20 mW–24 mW. Alternatively, blue light-emitting diodes (LED) with high output power may be used as the light source 302. Those skilled in the art will also recognize other suitable excitation light sources such as a broadband, incandescent light source from which a tunable, narrow band of excitation wavelengths can be selected by a diffraction grating or prism.

The excitation wavelength produced by light source 302 may be, for example, in the range of 470–490 nm, which is known to effectively excite the fluorophores tetramethylrhodamine isothiocyanate (TRITC) and fluorescein isothiocyanate (FITC). By binding the TRITC to concanavalin-A and the FITC to dextran, the concentration of glucose can be measured according to fluorescence resonance energy transfer process. When the FITC-dextran is bound to the TRITC-concanavalin-A, its fluorescence is quenched; glucose displaces the FITC-dextran, resulting in an increase in its fluorescence relative to that of the TRITC-concanavalin-A (as described by D. Meadows and J. Shultz, "Design, manufacture and characterization of an optical fiber glucose affinity sensor based on an homogeneous fluorescence energy transfer assay system," *Analytica Chimica Acta*, January 1993, 280:21–30). Of course, other excitation wavelengths and fluorescence changes may be used in methods of the invention, according to the sample 301 being tested (for example, W. P. Van Antwerp and J. J. Mastrototaro, U.S. Pat. No. 6,319,540, Nov. 20, 2001, herein incorporated by reference). The excitation light passes through a mounted dichroic mirror 312 and through a first fiber collimator 314, where it is focused. It then passes through optical connector 114, such as an AMP connector, which may be attached to the external end of the optical fiber 102 element of the biosensing device when a measurement is to be made. The light continues through the optical fiber 102 and to the internal end of the optical fiber 102. Upon excitation of any fluorophores present in the biosensing material, fluorescent wavelengths are emitted.

The fluorescent emissions are directed back through the optical fiber 102 and connector 114 to the information analyzer 112. For example, an excitation wavelength in the range of 470–490 nm will cause two emission wavelengths of 520 nm and 572 nm to be produced from the excited fluorophores FITC and TRITC, respectively, in the exemplary biosensing material for glucose described above. Where a single fiber is used, the fluorescent emission travels via the internal end of optical fiber 102 into the connector 114 and through the first fiber collimator 314 of the information analyzer. The fluorescent emission is deflected (for example 90°) by the dichroic mirror 312 into a filter system 304. For the exemplary process described above, in which two emission wavelengths are produced, the filter system could be, for example, a two-wavelength interference filter system that is mounted on a motorized, time-controlled filter wheel. The filter wheel mechanically alternates two interference filters to produce two narrowband signals centered at the emitted wavelengths. The narrowband signals are then focused at a second fiber collimator 305 and measured with a photo multiplier tube (PMT) detection system 306. For example, during a first interval, the excitation light intensity (488 nm) will produce a corresponding FITC fluorescence emission intensity (520 nm) that will be measured by detector system 306. During a second interval, the same excitation light intensity (488 nm) will produce a corresponding FITC fluorescence emission intensity (572 nm) that will be measured by detector system 306.

This cycle can be repeated numerous times when testing for analytes, and processed as described below. Alternatively, filter system 304 may employ optical grating filters within the filtering member 408. The application and manufacture of such grating regions within the filtering member 408 are discussed in further detail below.

Continuing with the description of FIG. 3, signal processing electronics 308 may, for example, compute the average and standard deviation for each sampling interval. The ratio (relative intensity) of the emission intensity of FITC at 520 nm to TRITC at 572 nm is then calculated and plotted as a function of analyte concentration. Results are displayed to the patient via a patient readout system 310 that may be, for example, an LED display, a numeric liquid crystal display or computer display located on a handheld information analyzer 112. The information can be displayed to the patient in various formats including, for example, alphanumeric readouts, on-screen icons or symbols, or various forms of graphs or charts.

Figure 4:
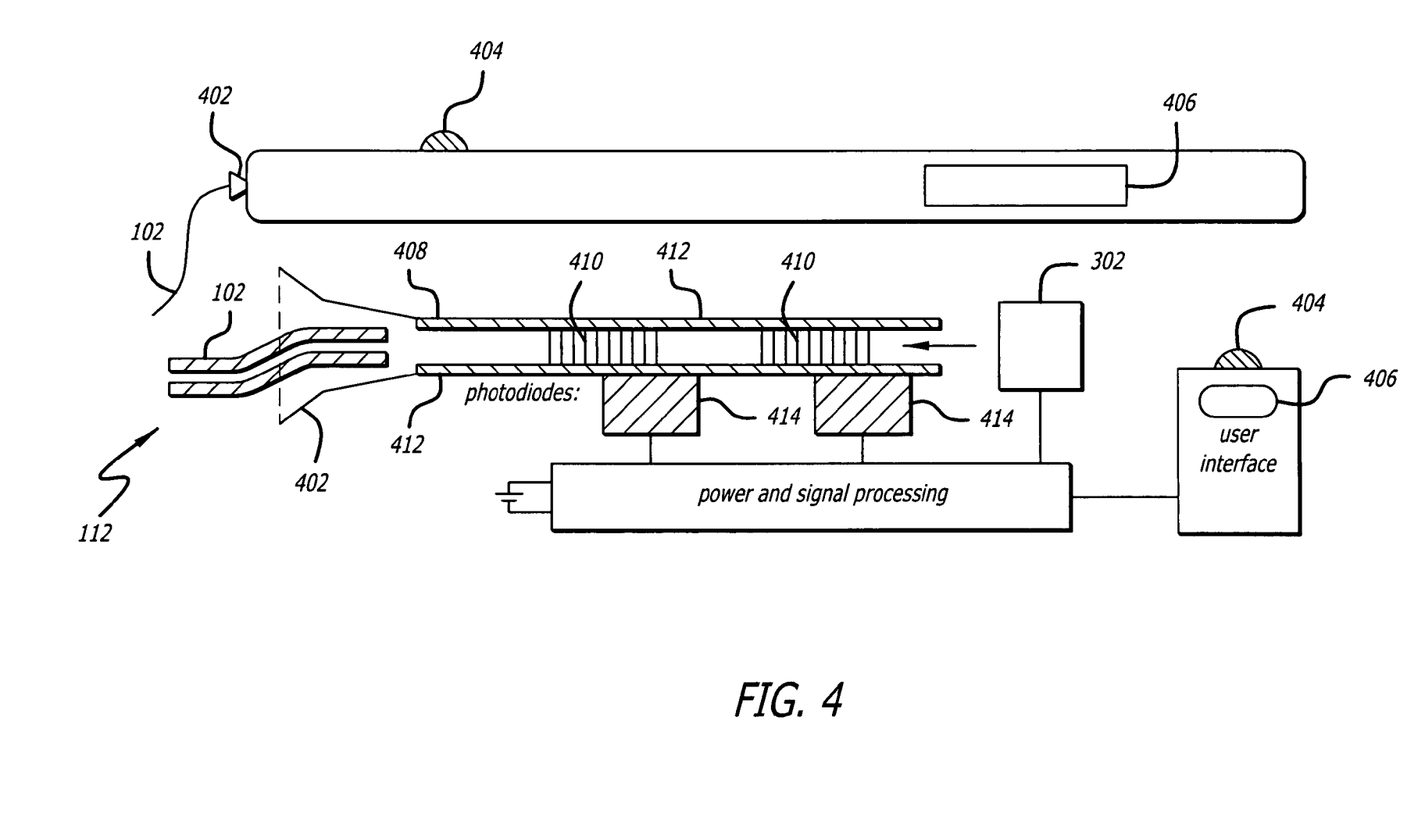
FIG. 4 illustrates an exemplary information analyzer configuration.

FIG. 4 illustrates an exemplary information analyzer 112 configuration that is sized and configured to be easily carried by the patient. The information analyzer 112 is portable such that it may be easily moved or even worn by the patient, sized and configured to be easily carried by the patient. For example, the information analyzer 112 could be sized to fit within a patient's hand, and could be light enough to be easily moved by the patient, or attached to the patient's clothing or to a strap that is worn by the patient. Because of its portability and small size, the information analyzer 112 may be used to take continuous measurements, such as when the patient wears it on his body or clothing. Its small size also makes the information analyzer 112 convenient for taking frequent, yet intermittent measurements, such as when the patient wears it or simply carries it with him because it is easily portable and accessible. In use, the patient slips the free external end of the optical fiber 102 of the implanted biosensing device into a connector 114, triggers a reading with a button 404 and views the results on a display 406. The conical orifice 402, in an exemplary embodiment, is a self-centering optical fiber connector, causing optical fiber 102 to be optically aligned with the filtering member 408 of the information analyzer 112.

As described in U.S. Pat. No. 6,058,226 (Starodubov), which is incorporated herein by reference, the filtering member 408, (which may also be an optical fiber), includes a tunable filter grating region 410 and a light source 302 such as a laser diode at one end. As fluorescent emissions from the fluorophore pass into the filter section 410, they are detected by detectors 414. In an exemplary embodiment, the filtering member 408 may also include a cladding layer 412, which could be, for example, a material similar in nature to the core of the optical fiber but with a different index of refraction. The cladding layer 412 is used to capture light that is deflected into it by the filtering member 408. Gratings in optical density within the filtering member 408 deflect photons with wavelengths matched to the grating wavelength into the cladding layer 412. Wavelengths traveling within the cladding layer 412 are captured and quantified by detectors 414 which may be, for example, photodiodes. Signal processing electronics 308 then receive information from detectors 414, analyze the information, and provide details to the patient by presenting them on display 406.

In manufacturing components for the information analyzer 112, the filtering member, which in the exemplary embodiment is optic fiber 408, is modified so that it contains alternating regions of higher and lower optical density at longitudinal intervals. These alternating regions of varying density create a wavelength specific optical grating within the filtering member 408. When light of a specific wavelength passes through that region of the fiber, it is deflected laterally into the cladding layer 412. This deflected light tends to continue propagating in the same longitudinal direction within the cladding, but it is highly deflected in the thin cladding layer and easily captured with a detector 414, such as a high efficiency photodiode, coupled to the side of the filtering member 408. Other wavelengths of light traveling through a given filter region of the filtering member 408 that is not tuned to those wavelengths pass without significant absorption or deflection. This makes it possible to design several adjacent optical gratings within the filtering member 408, each tuned to a different wavelength, to act as a series of high-Q spectral filters. Thus, multiple analytes can be detected using an information analyzer configured to selectively filter multiple wavelengths of emitted light from one another.

The tendency of light that is deflected into the cladding layer to have a weak longitudinal propagation is also advantageous when dealing with strong excitation light traveling in a direction opposite to the weak emission light to be detected. As will be recognized by those skilled in the art, carefully spacing the filter regions and photodiodes will minimize the detection of any excitation light that may be deflected into the cladding due to non-ideal properties of the filters.

Figures 5A, 5B, 6:
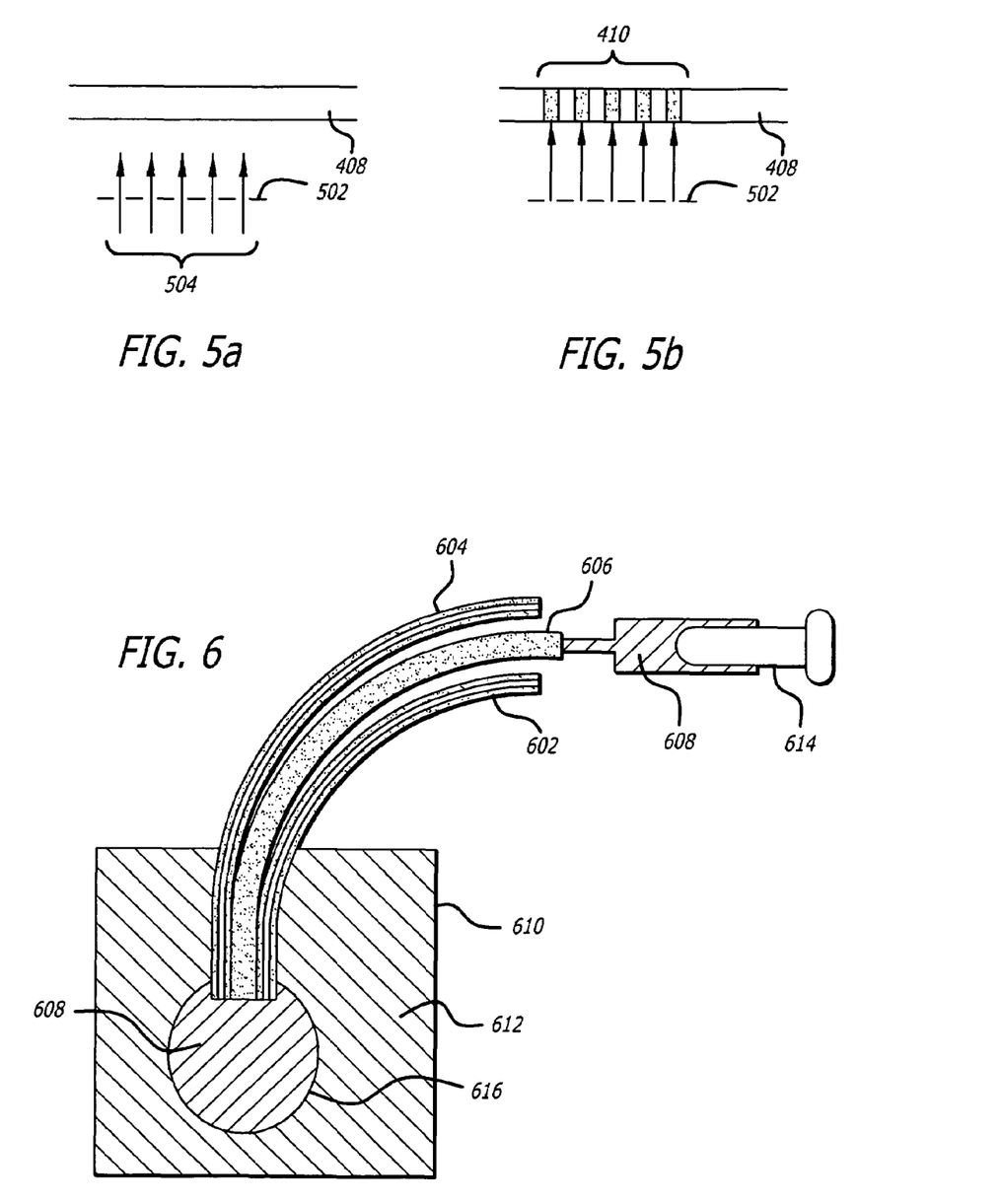
FIG. 6 illustrates an exemplary method for manufacturing a compact and portable biosensing device

FIGS. 5a and 5b illustrate an exemplary method for creating multiple tuned optical gratings within the filtering member 408 of the information analyzer 112. First, the filtering member 408 is made photo-sensitive by replacing some of the material with germanium. For example, in an embodiment having a silicon optical fiber 408, a portion of the silicon is replaced with germanium, which has photosensitive properties. Then, in FIG. 5a, an optical pattern 502 having the desired grating spacing is created by diffraction, and used to illuminate the fiber 408 from the side as indicated by arrows 504. The incident photons are absorbed by the germanium, precipitating a condensation in the local crystal lattice that changes its optical density, as illustrated in FIG. 5b. The pattern of this condensation becomes an optical grating region 410 within the filtering member 408. By this procedure, the filtering member 408 can be "photonically programmed" by brief exposure to patterned light to act as a custom multi-channel optical filter as required.

In use, to avoid damage to the optical fiber 102 of the implanted biosensing device during daily activities of the patient such as bathing and grooming, the external end of the fiber 102 in one embodiment is unencumbered by extraneous mechanical features. For example, connector 114 is attached to information analyzer 112 rather than to optical fiber 102. Optical fiber 102 is inserted into connector 114 only when a reading is to be taken. In one embodiment the connector 114 can be self-centering, such that optical fiber 102 is coaxially aligned with a mating optical fiber within information analyzer 112 in order to achieve adequate optical coupling. As shown in FIG. 4, this can be accomplished by shaping the orifice of connector 114 as a gradually tapering, truncated cone whose apical plane is formed by filtering member 408 that is made from an optical fiber having the same diameter as optical fiber 102. Also, some embodiments may involve the patient dipping the exposed end of the implanted optical fiber 102 into a combination cleaning and optical coupling solution before inserting it into the connector 114, to provide a fluid bridge between any physical gap that might remain between the transmitting and filtering members within the connector 114. Alternatively, connector 114 could be irrigated with a cleaning and optical coupling solution before optical fiber 102 is inserted into it. The optical coupling must be sufficient for the efficient transmission of excitation light directed toward biosensor element 110 and emission light received from biosensor element 110.

The various embodiments described herein may be constructed with a variety of different components and materials within the scope of the invention. For example, while various exemplary embodiments described above comprise a single optical fiber for transmitting light in two directions, it is also possible that a biosensing device or an information analyzer may utilize two separate transmitting members, each one propagating information in a single, different direction.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The biosensing device detects the presence of analytes within the patient's tissues by employing a biosensing material 116. A chemical binding or reaction between the analyte 108 and the biosensing material 116 gives rise to a state change that can be transmitted to and detected by the information analyzer 112. The biosensing material 116 preferably takes advantage of the unique specificity of biosensing molecules for analyte(s) of interest. This high selectivity allows the analyte to be measured even when mixed with other substances, such as occurs in blood or extracellular fluids. Ideally, the biosensor materials are selected to maintain mechanical stability and biocompatability during chronic implantation.

In an exemplary embodiment, the biosensing material 116 comprises an analyte-specific biomolecule immobilized in a polymer matrix which is in contact with the internal end of the transmitting member. In this embodiment, the biosensing material is presented at least on the surface of the polymer matrix, such that when analytes 108 diffuse into the region having the biosensing material 116, analytes 108 selectively bind with the biosensing material. The interaction of the analyte with the biosensing material results in a detectable state change. (i.e., changed fluorescent properties of the analyte, biosensing materials or reaction products.)

Receptors, antibodies, enzymes that specifically interact with the analyte(s) to be detected may be immobilized by physical capture within or covalent bonding to a biocompatible, polymeric matrix such as can be formed by the polymerization of various analogues of ethylene oxides to form, for example, polyethylene glycol. In one embodiment of the glucose biosensing material 116 described above, the TRITC-concanavalin-A is covalently bound to a polyethylene glycol that contains an N-hydroxysuccinimide ester group (PEG-NHS as described in the table with Example 1). The FITC-dextran is trapped within the small pores of the dense polyethylene glycol polymer, which is formed when polyethylene glycol diacrylate with molecular weight of 575 daltons is illuminated with ultraviolet light.

In one alternative embodiment, the biosensing material 116 may be fluidic or cellular in nature requiring encapsulation in a containment matrix (described below).

In another alternative embodiment, the biosensing material may include whole cells which are selected for or modified to respond to the selected analyte to produce a state change which is transmitted to and detected by the analyzer. For example, cells may be harvested from the patient (ex. endothelial cells) and modified for use as a biosensing material 116 by genetic engineering to cause them to express, for example, particular receptor molecules for the analyte 108 to be measured. Where the cells naturally express these molecules that interact selectively with the analyte 108 to be detected, these cells may be induced to take up fluorescent dyes that bind to these molecules and that change the intensity or wavelength of their fluorescence depending on the state of interaction between the molecules and the analyte 108.

Modification of cells may include transfecting the cells to express molecules which specifically react with the analyte of interest, as described, for example, in Tom Maniatis, "Molecular Cloning: a Laboratory Manual," 3rd Ed. For example, cells may be transfected with expression vectors encoding a receptor which selectively binds to the selected analyte. The receptor may be one located in the cell membrane (such as a transmembrane receptor), bound to the cell membrane (internal or external) or intracellular (e.g., lipid soluble analytes such as steroids).

Binding of the analyte to the receptor may then trigger a state change within the cells detectable by the information analyzer. For example, binding of an analyte (ex. hormone) to an expressed intracellular receptor may act as a transcription factor to enhance the expression of a second construct having a reporter (ex. luciferase) having fluorescent properties.

Modification of whole cells may also include dye loading. For example where the analyte selectively binds to a transmembrane receptor, the cell undergoes a sequence of chemical changes (i.e., ion fluxes) resulting in state changes which are detectable. For example, the changes could include opening of calcium channels through the cell membrane, increasing intracellular calcium, and the change in the fluorescence of a calcium sensitive dye (such as FURO-2) that has previously been loaded into cells.

The signal transduced in the biosensor device is thus a secondary one, due to the reaction between the biosensing molecules and target analyte. As indicated above, biosensing devices may employ several control and modulation methods: electrochemical, optical, thermal and mechanical. Turner A, Karube I and Wilson G. (1987) *Biosensors: Fundamentals and Applications*. London: Oxford Science Publications; Hall E. (1991) *Biosensors*. New Jersey: Prentice Hall; Fraser, D. (1997) *Biosensors in the body: continuous in vivo monitoring*. Chichester, N.Y.: Wiley; Blum, L. (1991) *Biosensor Principles and Applications*. New York: M. Dekker; Buck, R P. (1990) *Biosensor Technology: Fundamentals and Applications*. New York: M. Dekker, herein incorporated by reference.

In an exemplary embodiment fluorescence optical sensing is utilized. Here, the biosensing material includes molecules that undergo a change in fluorescent emission in proportion to the concentration of analyte of interest in the surrounding medium. For use in this system, many different fluorescent dyes have been developed and these can be bound covalently to molecules that bind specifically to analytes (such as glucose). Thompson, R. B. "Fluorescence-Based Fiber-Optic Sensors." *Topics in Fluorescence Spectroscopy*, Vol. 2: Principles. New York: Plenum Press 1991: 345–65; McNichols R and Cote G. "Optical glucose sensing in biological fluids: an overview." *Journal of Biomedical Optics* January 2000, 5:5–16; Czarnik, A. (1993) Fluorescent Chemosensors for Ion and Molecule Recognition. Washington: American Chemical Society, herein incorporated by reference. It is also within the scope of this invention to use other optical sensing techniques such as absorption and transmission which are well known to individuals skilled in the art.

Two particular alternatives are useful where fluorescence is selected as the mode of optical transmission: 1) the analyte is itself fluorescent; or 2) the analyte is not fluorescent but interacts with a fluorophore that emits a fluorescent signal. Krohn, D. (1988) Fiber Optic Sensors: Fundamentals and Applications. North Carolina: Instrument Society of America. Where the analyte to be detected is glucose, a number of techniques may be employed, including, but not limited to enzyme based and competitive affinity binding. McNichols R and Cote G. "Optical glucose sensing in biological fluids: an overview." *Journal of Biomedical Optics* January 2000, 5:5–16.

Many foreign molecules such as pharmacological agents can be detected by a fluorescence method that is based on affinity binding (immunoassay) between an antibody and an antigen. The antibody can be considered the molecular-recognition element (biosensing molecule), which binds reversibly with a specific antigen or analyte. Monoclonal antibodies are particularly useful because they provide a relatively pure source of a single antibody with a high affinity for a specific antigen. Monoclonal antibodies can be coupled to fluorescent dyes such as TRITC and FITC in such a way as to produce fluorescence whose intensity or wavelength is modulated depending on whether the antibody is bound to the antigen or not.

A containment matrix 120 may be useful in this invention. As mentioned, the materials of the containment matrix 120 are preferably selected to be biocompatible with the patient, permeable to the analytes being detected, minimally permeable to the reporting molecule being detected (i.e., fluorophores) and of a material which preferably forms a strong adhesion to the transmitting member in the absence or presence of additional adhesion coatings (described above). The containment matrix can be attached directly to the internal end of the transmitting member, permitting efficient and constant coupling to a small sensing structure. In an exemplary embodiment, polyethylene glycol (PEG) polymers are used as PEG demonstrates good biocompatability and structural integrity. Preferably, the polymer is applied to the transmitting member in an unpolymerized state, then polymerized to enhance stability of the structure by gamma irradiation, chemical cross-linking or UV radiation. One exemplary formula is described below.

In some cases, it may be possible to transmit both the exciting and emitted light over the same fiber, for example, if a brief excitation pulse of light produces a longer-lived lived fluorescence that an be detected after the excitation pulse has been extinguished. In other cases it may be necessary to have two optical fibers 102, one of which is used to transmit the excitation light inward while the outgoing fluorescent response is transmitted to a separate detector by the other. FIG. 6 illustrates an exemplary method for manufacturing a compact and portable biosensing device having a biosensing member surrounded by a containment matrix. The biosensing device could have, for example, at least two separate optical fibers 602 and 604 bundled together.

In some cases such as when the biosensing element 110 includes living cells, it may be necessary to retain the biosensing element 110 as a fluid on the internal end of the transmitting member 102. In the exemplary method depicted in FIG. 6, the transmitting member 102 contains a capillary tube 606. A suspension of biosensing material 608 may be prepared for injecting through the external end of the capillary tube 606 within an injector 614. The internal end of the assembly may be placed in a vacuum chamber 610 and exposed to vapor 612 of a vapor-depositable material. An exemplary polymer that could be used is Parylene-C (Registered trademark of Union Carbide Corp. for poly-monochloroparaxylylene), however those skilled in the art will recognize that a number of vapor-depositable material vapors may be employed. As the vapor 612 condenses and polymerizes on the surface of the bundle, a droplet of biosensing material 608 is injected through capillary tube 606 by injector 614, which can be, for example, a common hypodermic needle. The droplet cools rapidly by evaporation in the vacuum chamber 610. The low surface temperature of the rapidly cooling droplet causes a high rate of vapor condensation and polymerization, which forms containment matrix 616 around the droplet. Containment matrix 616 adheres to the optical fiber 602, forming a seal that retains biosensing material 608. If the analyte does not diffuse through the containment matrix 616, pores may be created through containment matrix 616 by various means such as laser ablation.

It will be obvious to those skilled in the art that other materials for the containment matrix are available, such as lipid or other semi permeable membranes that might not require the formation of pores therein. In an exemplary embodiment, membranes with special properties could be layered over the biosensing material 116, for example semipermeable or ion selective membranes may be used to form a containment matrix 118. In this example, the ratio of the cross-sectional area of the pore 120 to the volume of the biosensing material 116 may function as a preset control on the rate at which the analyte enters the sensing area through the containment matrix 118. This particular embodiment may be useful for quantitative assays of small molecules by non-cellular biosensor materials such as enzymes or antibodies, e.g., glucose sensor for diabetics. See for example, U.S. Pat. No. 6,063,637 to Arnold et al., herein incorporated by reference.

It will be recognized that alternative embodiments of the biosensing device will require alternative manufacturing processes. For example, in an exemplary embodiment involving cells as the biosensing material 508, the cells may be grown onto the tip of an optical fiber 502 in tissue culture. When the tip of the optical fiber 502 is removed from the aqueous culture medium, a droplet of cells and media cling to the tip and may then be coated with condensed vapor 512 according to a cooling and condensing method as described above.

The biosensing material of the invention is designed for implantation subcutaneously into a well-vascularized space (such as the scalp). However, it should be noted that intravascular and implantation within an organ may be desirable for measuring some analytes. Preferably the transmitting member is also implanted at least partially subcutaneously for local detection (such as photonic detection) from the biosensing material. The biosensing materials and transmitting member are preferably constructed so as to remain stably positioned within a patient's body for repeated measures of analyte for a selected time, such as at least one to three months or longer. However, the biosensor and transmitting member are also preferably constructed and implanted so as to be wholly and completely removable from the patient when the biosensor is no longer functioning or required. Alternatively, the biosensing element 110 may be constructed so as to detach from the transmitting member during its removal and to biodegrade in situ. The close coupling afforded between the optical fiber and the biosensor permit the volume of the biosensor to be very small, reducing the possibility of a toxic or immunogenic reaction to the biosensing element 110 as it degrades.

In an exemplary embodiment such as shown in FIG. 1 or 2, the outer surface of the transmitting member 102 may be modified such that various coatings may be applied to regions of the outer surface of the member. Coatings which improve biocompatibility with patient tissues generally and integration with the skin are desirable so that a long-lived stable interface is formed between the transmitting member and the body. Any selected portion of the transmitting member 102 (such as the region of the transmitting member 122 passing through the skin 104) or the entire length of the fiber may be coated with substances which promote cellular attachment. For example, the transmitting member may be coated with a naturally occurring protein, collagen to encourage a stable percutaneous interface (U.S. Pat. No. 5,800,545 to Yamada et al., Sep. 1, 1998, incorporated herein by reference). Example 1 below describes the surface modification of a glass optical fiber by acylation in an acrylol chloride solution, thereby providing a covalent binding site for attachment of the acrylate group of the polyethylene glycol. This and similar adhesion promoters can be used to attach firmly coatings to the optical fiber that provide stable, biocompatible attachment to the skin. Such coatings may be prepared in layers, such as an inner covalent binding site on the optical fiber, a hydrogel polymer such as polyethylene glycol bound to the binding sites, and a layer of collagen or other naturally occurring protein attached to the polymer that becomes integrated into the surrounding tissues of the skin.

Further, it may desirable to apply coatings to the outer surface of the transmitting member 102 to enhance the attachment of the biosensing material 116 and/or the containment matrix 118 thereto. These coatings are desirable to encourage a stable interface between the transmitting member and the biosensing material such that these components of the device remain in operative communication. Further these coatings are desirable to encourage a stable interface between the transmitting member and the containment matrix, so that where desired, the biosensing material is isolated from the patient tissue and reaction products are maintained in a concentrated area for detection. Finally, a stable interface is desirable such that when the device is removed from the patient it can be removed as a single structure. As shown in the exemplary embodiment of FIG. 2, the transmitting member internal end 124 may be coated for these purposes. Where containment matrix 118 is formed of substantially polyethylene glycol (PEG), a silicon outer surface of the transmitting member 102 may be prepared with a commercial trichlorosilane as an adhesion promoter. Where a plastic transmitting member 102 is used, their typical Teflon outer jacket provides a surface that binds tightly to PEG derivatives that have been end-functionalized with 1–4 perfluorocarbon groups that have been shown to strongly adsorb physically to Teflon surfaces (Hogen-Esch, T. E.; Zhang, H.; Xie, X. "Synthesis and Characterization of Well Defined End-Functionalized Hydrocarbon and Perfluorocarbon Derivatives of Polyethyleneglycol and Poly(N.N-dimethylacrylamide), Chapter 11, in "Associative Polymers in Aqueous Solutions," ACS Symposium Series Vol. 765, pp. 179–203, J. E. Glass Editor, 2000). Covalent binding can also be obtained to either surface by glow-discharge pretreatment of the fiber surface. Wang, P. Tan, K. L. and Kang. E. T. "Surface modification of poly(tetrafluoroethylene) films via grating of poly(ethylene glycol) for reduction in protein adsorption." *Journal of Biomedical Science and Polymer* Edition. 2000, 11:169–186. A glass optical fiber 102 can be pretreated with Ar plasma before graft copolymerization and then exposed to the atmosphere for about 10 min to effect the formation of the surface peroxides and hydroperoxides. The peroxide will form a covalent bonding with the acrylate group of PEG.

EXAMPLE 1

Material and Method of Forming a Biosensor Element

Note that the outer layer described and the method of preparing the outer layer described (in steps 3 and 5, for example) are optional. The outer layer may be desirable where it is desired to prevent the inner PEG layer (having reactants and fluorophores) from being directly exposed to the patient's tissue.

A. Composition of polyethylene glycol hydrogel inner and outer layer, including an exemplary sensing system for measurement of glucose by competitive binding of fluorophores.

|  | Inner PEG Layer (w/w) | Outer PEG Layer (w/w) |
|---|---|---|
| PEG-DA 575 (polyethylene glycol-diacrylate) | 32.06% | 32.15% |
| PEG-NHS 3400 (a-acryloyl,ω-N-hydroxysuccimidyl ester of poly(ethylene glycol)-propionic acid, Con A immobilized) | 0.16% | none |
| TRITC-Con A/FITC-dextran (100/1) | 0.13% | none |
| DMPA (2,2-dimethoxy-2-phenyl acetophenone, radical initiator) | 0.32% | 0.32% |

-continued

|  | Inner PEG Layer (w/w) | Outer PEG Layer (w/w) |
|---|---|---|
| TPT (trimethylol propane triacrylate, Cross-linking agent to form copolymer hydrogel for the sake of stability of hydrogel) | 3.2% | 3.3% |
| PBS (phosphate buffer system, pH 7.4, 0.1 M) | 64.12% | 64.31% |

B. Method of Manufacture

1: Conjugation of TRITC-Con A (This provides the concanavalin-A, which competitively binds glucose and dextran, with the TRITC fluorophore; adapted from R. M. McKinney, J. T. Spillane, G. W. Pearce, 1966, "A Simple Method for Determining the Labeling Efficiency of Fluorescein Isothiocyanate Products", Analytical Biochemistry 14:421–428). TRITC 2 mg/ml is made to volume with pH 8.0, 0.1M sodium phosphate buffer. 5 ml of the TRITC sample is added into 2 ml of 5% Con A solution, and sufficient PBS buffer will be added to give a total of 10 ml. The reaction mixture is allowed to stand overnight or about 16 hrs. to ensure complete reaction. The reaction mixture is then poured into a dialysis bag, and placed in a beaker full of buffer solution. The buffer outside the bag is changed daily until substantially no fluorescent material is present in the buffer solution.

2: Preparation of inner layer precursor solution (This combines the PEG carrier with the TRITC-Con A and FITC-dextran fluorophores; adapted from R. J. Russell, M. V. Pishko, C. C. Gefrides, M. J. McShane and G. L. Cote, 1999, "A Fluorescence-Based Glucose Biosensor Using Concanavalin A and Dextran Encapsulated in a Poly(ethylene glycol) Hydrogel", Anal. Chem 71:3126–3132). FITC-dextran is dissolved immediately prior use in 0.1M PBS (pH 7.4) at a concentration of 10 mg/ml. TRITC-Con A solution (TRITC-Con A/FITC-dextran=100/1) and PEG-NHS (TRITC-Con A/PEG-NHS=100 µL/1 mg) is added to PEG-DA (volume ratio of PEG-DA to fluorescein solution is 2:1) and the resultant mixture is vortexed for 30 min. FITC-dextran (TRITC-Con A/FITC-dextran=100/1), 100 µL of TPT, and 10 mg DMPA will be added and vortexed for 30 min.

3. Preparation of outer layer precursor solution. 100 µL of TPT, and 10 mg DMPA, PBS is added to PEG-DA to reach the ratio 2 to 1 in volume and vortexed for 30 min.

4. Activation of optical fiber surface and attachment of inner carrier layer (adopted from the method of C. Munkholm, D. R. Walt, F. P. Milanovich and S. M. Klainer, 1986, "Polymer Modification of Fiber Optic Chemical Sensors as a Method of Enhancing Fluorescence Signal for pH Measurement", Anal. Chem, 58:1427–1430). 10% aqueous solution of (aminopropyl)triethoxysilane is adjusted to pH 3.45. Fibers are submerged and placed in a 75° C. water bath for 3 hours. Then rinsed with water and dried overnight in the oven at 95° C. The modified fibers are placed into a solution of acrylol chloride and allowed to rest for 1 h in the dark. The fibers are sensitized by soaking for 10 min in a benzophenone/cyclohexane solution (0.93 g/5 ml). Fiber tips are dipped into the unpolymerized hydrogel inner layer precursor solution and removed. The volume of droplet left hanging is dependant on the depth of immersion and surface tension (which is, in turn, related to experimentally manipulatable factors, including viscosity of the solution and surface properties of the fiber). Fiber tips are then exposed to UV light, for example to polymerize PEG.

5. Cross-linking of outer layer hydrogel and attachment. The fiber tip is immersed into hydrogel outer layer precursor solution and exposed to UV to initiate cross-linking. Alternatively, chemical activation may also be employed.

EXAMPLE 2

Fluorescence Resonance Energy Transfer Phenomenon as Applied to an Affinity Binding Assay System for Glucose Sensing This example describes the fluorescence transduction techniques based the affinity binding assay system for polysaccharides based on the jack bean lectin concanavalin A (ConA). Mansouri S, Schultz J. "A Miniature Optical Glucose Sensor Based on Affinity Binding." *Biotechnology* 1984, 885–90. This system uses a biosensor based on competitive binding between glucose and dextran. The assay aqueous solution is encapsulated within a hollow dialysis membrane permeable to glucose. In the assay, Con A is used as a receptor for competing species of fluorescein isothiocyanate (FITC) labeled dextran and glucose. FITC-dextran reversibly binds to Con A; as glucose concentration increases, FITC-dextran is displaced from ConA receptor sites, thus increasing the concentration and measurable fluorescence intensity of FITC-dextran.

Also, fluorescence resonance energy transfer (FRET), which is based on molecular proximity of donor and acceptor molecules is relevant to fluorescent detection. Here, individual molecules are labeled with fluorophores or dyes. When a donor dye and an acceptor dye are within a certain distance known as Forster distance (20–70 Å) from each other, dipole-dipole interactions between these molecules result in "fluorescence quenching" or reduction of the fluorescence of the donor molecule. Conversely, when these molecules are more than 70 Å apart, the quenching is reduced as the interchromophore distance increases, resulting in an increase in the measured fluorescence intensity of the donor molecule. There are many donor-acceptor fluorophores that are applicable for use in FRET applications. Based on the availability of labeling protocols for these dyes, including, but not limited to fluorescein isothiocyanate (FITC) and tetramethylrhodamine isothiocyanate (TRITC). FITC has an excitation peak centered at 488 nm and an emission peak at 520 nm, and TRITC (by itself) has an excitation peak at 540 nm and an emission peak at 580 nm.

Dextran is labeled with FITC (fluorescer) and Con-A is labeled with TRITC (quencher). When TRITC-ConA is added to a solution of FITC-Dextran, the binding of the dextran to ConA results in the required molecular proximity (5.4 nm) for FRET-based based quenching to occur. FITC-Dextran reversibly binds to TRITC-ConA, and FITC transfers electrons to TRITC, thereby resulting in the quenching of the fluorescein signal (low fluorescence). As glucose is added to the system, FITC-Dextran is displaced from the TRITC-ConA, resulting in increased fluorescein signal (high fluorescence intensity) upon excitation at 488 nm. The signal emitted at 520 nm is then detected and converted to quantitative information by an intensity-based fluorescence spectrophotometer normalized at 572 nm. The ratio of fluorescence intensity at the two wavelengths can be used to infer glucose concentration.

EXAMPLE 3

Clinical Analytes for which the Biosensing Device may be Configured to Detect, Include, but are not Limited to:

| Biological Elements | Analytes |
| --- | --- |
| Enzymes/Metabolites | glucose, cholesterol, amylase, urea, triglycerides pH, Na+, Ca2+, K+, H+, Cl−, HCO3, Fe, NH3 Creatinine kinase, Creatinine, Aspartate amino-transferase, Phenylalanine, Lactate dehydrogenase, Akaline phosphotase, GOT, Bilirubin |
| Gases | oxygen, carbon dioxide, ammonia |
| Therapeutic Drugs | Salicylate, Acetaminophen (paracetamol), Ethanol, Theophylline, Dilantin, Gentamicin, Tobramicin, Digoxin cortisol, estriol, pro- |
| Hormones | gesterone, aldosterone, cortisone, thyroxine binding globulin, placental lactogen, prolactin, human chorionic gonadotropin, insulin, parathyroid hormone, growth hormone, angiotensin, oxytocin, vasopressin |
| Antibodies | IgM (total), IgG (specific), Syphilis, Rubella |
| Antigens | A & B, Rh, Hepatitis, Alpha-fetoprotein, various cancer proteins |

Hall E. (1991) Biosensors. New Jersey: Prentice Hall.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method of manufacturing a component for use in a biosensing device for detecting one or more analytes, including:

providing a transmitting member having a first end and a second end, the second end being configured for operably coupling to an information analyzer, wherein the transmitting member comprises at least a capillary tube having a lumen and an optical fiber, and wherein biosensing materials are applied to the transmitting member first end by injection of the biosensing materials to a capillary tube first end and through the lumen to a capillary tube second end;

applying a biosensing element having one or more biosensing materials to the transmitting member first end; and applying a containment matrix to the transmitting member first end wherein the containment matrix substantially surrounds the biosensing materials and wherein the containment matrix is permeable to an analyte to be detected.

2. A device for detecting an analyte from within a patient's body comprising:

biosensing material;

at least one optical fiber having a first and a second end, wherein the first end is attached to the biosensing material and the second end is unencumbered by external mechanical features; and a capillary tube having a first end attached to the biosensing material and a second end adapted to interface with a biosensing material-injection device.

3. The device of claim 2, further comprising a portable measuring instrument configured to optically couple to the second end of the optical fiber in a releasable manner.

4. The device of claim 3 wherein: the biosensing material includes a fluorescing molecule; and the portable measuring instrument is configured to cause the fluorescing molecule in the vicinity of the biosensing material to fluoresce and to detect the fluorescence from the fluorescing molecule.

5. The device of claim 3, wherein the portable measuring instrument further comprises an optical connector.

6. The device of claim 5, wherein the portable measuring instrument further comprises a mating optical fiber.

7. The device of claim 6, wherein the optical connector of the portable measuring instrument is configured to cause the second end of the optical fiber to be coaxially aligned with the mating optical fiber.

8. The device of claim 5, wherein optical connector is conical.

9. The device of claim 2 further comprising a containment matrix enclosing the biosensing material.

10. The device of claim 9 wherein the containment matrix is affixed to the first end of the optical fiber.

* * * * *